United States Patent
Zhou

(10) Patent No.: US 8,137,083 B2
(45) Date of Patent: Mar. 20, 2012

(54) INFUSION PUMP ACTUATORS, SYSTEM AND METHOD FOR CONTROLLING MEDICAL FLUID FLOWRATE

(75) Inventor: Yu Zhou, Vernon Hills, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 284 days.

(21) Appl. No.: 12/402,255

(22) Filed: Mar. 11, 2009

(65) Prior Publication Data

US 2010/0229978 A1 Sep. 16, 2010

(51) Int. Cl.
- F04B 43/08 (2006.01)
- F04B 45/06 (2006.01)
- F01B 19/04 (2006.01)
- A61M 1/00 (2006.01)

(52) U.S. Cl. .............. 417/478; 92/92; 604/153

(58) Field of Classification Search ............. 417/474, 417/476, 477.1, 477.3, 477.5, 477.7, 477.8, 417/477.6, 478, 481, 479; 92/90, 91, 92; 74/110, 520; 604/131, 151, 153
See application file for complete search history.

(56) References Cited

U.S. PATENT DOCUMENTS

| | | | | |
|---|---|---|---|---|
| 685,385 A * | 10/1901 | Odette | | 254/31 |
| 1,893,776 A * | 1/1933 | Hull | | 417/478 |
| 2,757,554 A * | 8/1956 | Niedhammer, Jr. et al. | | 74/520 |
| 3,606,596 A | 9/1971 | Edwards | | |
| 3,756,752 A | 9/1973 | Stenner | | |
| 3,771,694 A | 11/1973 | Kaminski | | |
| 3,809,191 A * | 5/1974 | Woodward | | 188/106 A |
| 3,809,871 A | 5/1974 | Howard et al. | | |
| 3,998,103 A | 12/1976 | Bjorklund et al. | | |
| 4,038,983 A | 8/1977 | Mittleman et al. | | |
| D246,258 S | 11/1977 | Ekert | | |
| 4,065,230 A | 12/1977 | Gezari | | |
| 4,078,562 A | 3/1978 | Friedman | | |
| 4,151,407 A | 4/1979 | McBride et al. | | |
| 4,187,057 A | 2/1980 | Xanthopoulos | | |
| 4,199,307 A | 4/1980 | Jassawalla | | |

(Continued)

FOREIGN PATENT DOCUMENTS

EP 0215249 3/1987

(Continued)

OTHER PUBLICATIONS

International Search Report for International Application No. PCT/US 02/36963 of Applicant Baxter International Inc., Dated 2003.

(Continued)

*Primary Examiner* — Devon C Kramer
*Assistant Examiner* — Bryan Lettman
(74) *Attorney, Agent, or Firm* — K&L Gates LLP

(57) ABSTRACT

An infusion pump includes an actuator having an output shaft; a pump actuator having a length ($l_{actuator}$) moved by the output shaft and in contact with tubing, such that the pump actuator at an output shaft actuated distance (x) creates flat contact areas with the tubing, and wherein remaining non-contact areas of the tubing are at least substantially circular in shape; and a logic implementer configured to use at least two relationships to solve for a same number of variables to calculate a cross-sectional area of the tubing at an output shaft actuated distance (x).

22 Claims, 5 Drawing Sheets

U.S. PATENT DOCUMENTS

| | | | |
|---|---|---|---|
| 4,237,409 A | 12/1980 | Sugalski | |
| 4,256,437 A | 3/1981 | Brown | |
| 4,273,121 A | 6/1981 | Jassawalla | |
| 4,276,004 A | 6/1981 | Hahn | |
| 4,277,226 A | 7/1981 | Archibald | |
| 4,308,866 A | 1/1982 | Jelliffe et al. | |
| 4,320,757 A | 3/1982 | Whitney et al. | |
| D263,997 S | 4/1982 | Preussner | |
| 4,332,246 A | 6/1982 | Thomson | |
| 4,369,780 A | 1/1983 | Sakai | |
| 4,373,525 A | 2/1983 | Kobayashi | |
| D268,206 S | 3/1983 | Kosako | |
| 4,392,849 A | 7/1983 | Petre et al. | |
| 4,398,908 A | 8/1983 | Siposs | |
| 4,416,595 A | 11/1983 | Cromie | |
| 4,428,381 A | 1/1984 | Hepp | |
| 4,430,078 A | 2/1984 | Sprague | |
| 4,443,216 A | 4/1984 | Chappell | |
| 4,445,535 A | 5/1984 | Mayfield | |
| 4,447,233 A | 5/1984 | Mayfield | |
| 4,447,234 A | 5/1984 | Mayfield | |
| 4,451,255 A | 5/1984 | Bujan et al. | |
| 4,457,751 A | 7/1984 | Rodler | |
| 4,460,358 A | 7/1984 | Somerville et al. | |
| 4,468,221 A | 8/1984 | Mayfield | |
| 4,472,116 A | 9/1984 | Wenstrup | |
| 4,487,604 A | 12/1984 | Iwatschenko et al. | |
| 4,493,710 A | 1/1985 | King et al. | |
| 4,496,351 A | 1/1985 | Hillell et al. | |
| 4,498,843 A | 2/1985 | Schneider et al. | |
| D278,181 S | 3/1985 | Archibald et al. | |
| 4,504,200 A | 3/1985 | Olson | |
| 4,511,352 A | 4/1985 | Theeuwes et al. | |
| D278,743 S | 5/1985 | Manno et al. | |
| 4,519,792 A | 5/1985 | Dawe | |
| 4,529,401 A | 7/1985 | Leslie et al. | |
| 4,537,561 A | 8/1985 | Xanthopoulos | |
| 4,544,369 A | 10/1985 | Skakoon et al. | |
| 4,551,133 A | 11/1985 | Zegers de Beyl et al. | |
| 4,559,038 A | 12/1985 | Berg et al. | |
| 4,561,830 A | 12/1985 | Bradley | |
| 4,561,856 A | 12/1985 | Cochran | |
| 4,562,751 A | 1/1986 | Nason et al. | |
| 4,565,542 A | 1/1986 | Berg | |
| 4,585,009 A | 4/1986 | Barker et al. | |
| 4,585,941 A | 4/1986 | Bergner | |
| 4,596,550 A | 6/1986 | Troutner | |
| 4,601,702 A | 7/1986 | Hudson | |
| 4,602,249 A | 7/1986 | Abbott | |
| 4,624,661 A | 11/1986 | Arimond | |
| D287,053 S | 12/1986 | Bucchianeri et al. | |
| D287,277 S | 12/1986 | Kosako et al. | |
| 4,637,817 A | 1/1987 | Archibald et al. | |
| 4,639,245 A | 1/1987 | Pastrone et al. | |
| 4,646,781 A | 3/1987 | McIntyre et al. | |
| 4,648,812 A | 3/1987 | Kobayashi et al. | |
| 4,650,469 A | 3/1987 | Berg et al. | |
| 4,652,262 A | 3/1987 | Veracchi | |
| 4,653,987 A | 3/1987 | Tsuji et al. | |
| 4,657,490 A | 4/1987 | Abbott | |
| 4,666,430 A | 5/1987 | Brown et al. | |
| 4,668,220 A | 5/1987 | Hawrylenko | |
| 4,676,776 A | 6/1987 | Howson | |
| 4,678,408 A | 7/1987 | Nason et al. | |
| 4,681,563 A | 7/1987 | Deckert et al. | |
| 4,685,903 A | 8/1987 | Cable et al. | |
| 4,690,673 A | 9/1987 | Bloomquist | |
| 4,696,671 A | 9/1987 | Epstein et al. | |
| D293,468 S | 12/1987 | Hill et al. | |
| 4,714,462 A | 12/1987 | DiDomenico | |
| 4,718,576 A | 1/1988 | Tamura et al. | |
| 4,718,893 A | 1/1988 | Dorman et al. | |
| 4,722,149 A | 2/1988 | Weaver et al. | |
| 4,722,224 A | 2/1988 | Scheller et al. | |
| 4,722,734 A | 2/1988 | Kolln | |
| 4,725,205 A | 2/1988 | Cannon et al. | |
| 4,731,058 A | 3/1988 | Doan | |
| D295,320 S | 4/1988 | Vaughan | |
| 4,741,732 A | 5/1988 | Crankshaw et al. | |
| 4,741,736 A | 5/1988 | Brown | |
| 4,744,786 A | 5/1988 | Hooven | |
| 4,754,401 A | 6/1988 | Kaczynski et al. | |
| 4,756,706 A | 7/1988 | Kerns et al. | |
| 4,758,228 A | 7/1988 | Williams | |
| 4,759,527 A | 7/1988 | Brown | |
| 4,772,263 A | 9/1988 | Dorman et al. | |
| 4,781,548 A | 11/1988 | Alderson et al. | |
| 4,804,368 A | 2/1989 | Skakoon et al. | |
| 4,810,243 A | 3/1989 | Howson | |
| 4,834,704 A | 5/1989 | Reinicke | |
| 4,836,752 A | 6/1989 | Burkett | |
| 4,838,857 A | 6/1989 | Strowe et al. | |
| 4,838,860 A | 6/1989 | Groshong et al. | |
| 4,840,542 A | 6/1989 | Abbott | |
| 4,846,637 A | 7/1989 | Alderson et al. | |
| 4,854,324 A | 8/1989 | Hirschman et al. | |
| 4,856,339 A | 8/1989 | Williams | |
| 4,882,575 A | 11/1989 | Kawahara | |
| D305,060 S | 12/1989 | Bisha' et al. | |
| 4,886,431 A | 12/1989 | Soderquist et al. | |
| 4,890,984 A | 1/1990 | Alderson et al. | |
| 4,898,579 A | 2/1990 | Groshong et al. | |
| 4,900,305 A | 2/1990 | Smith et al. | |
| 4,908,017 A | 3/1990 | Howson et al. | |
| 4,911,168 A | 3/1990 | Davis | |
| 4,919,650 A | 4/1990 | Feingold et al. | |
| 4,923,375 A | 5/1990 | Ejlersen | |
| 4,931,041 A | 6/1990 | Faeser | |
| 4,936,760 A | 6/1990 | Williams | |
| D309,662 S | 7/1990 | Gorton | |
| 4,941,808 A | 7/1990 | Qureshi et al. | |
| 4,943,279 A | 7/1990 | Samiotes et al. | |
| 4,954,046 A | 9/1990 | Irvin et al. | |
| 4,960,230 A | 10/1990 | Marelli | |
| 4,976,151 A | 12/1990 | Morishita | |
| 4,978,335 A | 12/1990 | Arthur, III | |
| 5,000,739 A | 3/1991 | Kulisz et al. | |
| 5,006,050 A | 4/1991 | Cooke et al. | |
| 5,011,378 A | 4/1991 | Brown et al. | |
| 5,017,192 A | 5/1991 | Dodge et al. | |
| 5,018,945 A * | 5/1991 | D'Silva | 417/12 |
| 5,034,004 A | 7/1991 | Crankshaw | |
| 5,041,086 A | 8/1991 | Koenig et al. | |
| 5,044,900 A | 9/1991 | Cavallaro | |
| 5,049,047 A | 9/1991 | Polaschegg et al. | |
| 5,053,031 A | 10/1991 | Borsanyi | |
| 5,055,001 A | 10/1991 | Natwick et al. | |
| 5,057,081 A | 10/1991 | Sunderland et al. | |
| 5,061,243 A | 10/1991 | Winchell et al. | |
| D321,559 S | 11/1991 | Kienholz | |
| 5,078,362 A | 1/1992 | Lawless et al. | |
| 5,078,683 A | 1/1992 | Sancoff et al. | |
| 5,080,653 A | 1/1992 | Voss et al. | |
| 5,088,904 A | 2/1992 | Okada | |
| 5,098,256 A | 3/1992 | Smith | |
| 5,098,377 A | 3/1992 | Borsanyi et al. | |
| 5,100,380 A | 3/1992 | Epstein et al. | |
| 5,100,389 A | 3/1992 | Vaillancourt | |
| 5,102,392 A | 4/1992 | Sakai et al. | |
| 5,104,374 A | 4/1992 | Bishko et al. | |
| D326,153 S | 5/1992 | Eastman et al. | |
| 5,116,203 A | 5/1992 | Natwick et al. | |
| 5,120,096 A | 6/1992 | D'Silva | |
| 5,123,275 A | 6/1992 | Daoud et al. | |
| 5,131,816 A | 7/1992 | Brown et al. | |
| D328,952 S | 8/1992 | Arioka | |
| 5,135,500 A | 8/1992 | Zdeb | |
| 5,139,390 A * | 8/1992 | Rajewski | 417/53 |
| 5,153,827 A | 10/1992 | Coutre et al. | |
| 5,160,320 A | 11/1992 | Yum et al. | |
| 5,165,874 A | 11/1992 | Sancoff et al. | |
| 5,167,633 A | 12/1992 | Mann et al. | |
| 5,176,004 A | 1/1993 | Gaudet | |
| 5,176,644 A | 1/1993 | Srisathapat et al. | |
| 5,181,842 A | 1/1993 | Sunderland et al. | |
| 5,181,910 A | 1/1993 | Scanlon | |
| 5,197,322 A | 3/1993 | Indravudh | |

| | | |
|---|---|---|
| 5,207,645 A | 5/1993 | Ross et al. |
| 5,213,483 A | 5/1993 | Flaherty et al. |
| 5,217,442 A | 6/1993 | Davis |
| 5,219,327 A | 6/1993 | Okada |
| 5,219,330 A | 6/1993 | Bollish et al. |
| 5,219,331 A | 6/1993 | Vanderveen |
| 5,219,428 A | 6/1993 | Stern |
| 5,232,449 A | 8/1993 | Stern et al. |
| 5,236,416 A | 8/1993 | McDaniel et al. |
| 5,238,001 A | 8/1993 | Gallant et al. |
| D339,193 S | 9/1993 | Thompson et al. |
| 5,242,407 A | 9/1993 | Struble et al. |
| 5,242,408 A | 9/1993 | Jhuboo et al. |
| 5,244,461 A | 9/1993 | Derlien |
| 5,244,463 A | 9/1993 | Cordner, Jr. et al. |
| 5,254,096 A | 10/1993 | Rondelet et al. |
| 5,256,157 A | 10/1993 | Samiotes et al. |
| 5,257,971 A | 11/1993 | Lord et al. |
| 5,261,884 A | 11/1993 | Stern et al. |
| 5,265,431 A | 11/1993 | Gaudet et al. |
| D342,231 S | 12/1993 | Walker et al. |
| 5,276,610 A | 1/1994 | Maeda et al. |
| 5,279,556 A | 1/1994 | Goi et al. |
| 5,281,111 A | 1/1994 | Plambeck et al. |
| 5,290,239 A | 3/1994 | Classey et al. |
| 5,295,966 A | 3/1994 | Stern et al. |
| 5,295,967 A | 3/1994 | Rondelet et al. |
| 5,298,021 A | 3/1994 | Sherer |
| D347,472 S | 5/1994 | Sunderland et al. |
| 5,308,333 A | 5/1994 | Skakoon |
| 5,308,335 A | 5/1994 | Ross et al. |
| 5,317,506 A | 5/1994 | Coutre et al. |
| D348,101 S | 6/1994 | Poli et al. |
| 5,321,392 A | 6/1994 | Skakoon et al. |
| D348,730 S | 7/1994 | Walker et al. |
| 5,326,236 A | 7/1994 | Kramer et al. |
| 5,328,460 A | 7/1994 | Lord et al. |
| 5,330,431 A | 7/1994 | Herskowitz |
| 5,336,245 A | 8/1994 | Adams et al. |
| 5,338,157 A | 8/1994 | Blomquist |
| 5,341,291 A | 8/1994 | Roizen et al. |
| 5,343,734 A | 9/1994 | Maeda et al. |
| 5,348,539 A | 9/1994 | Herskowitz |
| 5,356,379 A | 10/1994 | Vaillancourt |
| D352,778 S | 11/1994 | Irvin et al. |
| 5,366,904 A | 11/1994 | Qureshi et al. |
| D353,667 S | 12/1994 | Tsubota et al. |
| 5,370,612 A | 12/1994 | Maeda et al. |
| 5,370,622 A | 12/1994 | Livingston et al. |
| 5,374,251 A | 12/1994 | Smith |
| 5,374,965 A | 12/1994 | Kanno |
| 5,376,070 A | 12/1994 | Purvis et al. |
| 5,378,231 A | 1/1995 | Johnson et al. |
| 5,382,236 A | 1/1995 | Otto et al. |
| D355,716 S | 2/1995 | Nash et al. |
| 5,387,088 A | 2/1995 | Knapp et al. |
| 5,389,078 A | 2/1995 | Zalesky et al. |
| 5,395,320 A | 3/1995 | Padda et al. |
| 5,395,324 A | 3/1995 | Hinrichs et al. |
| 5,395,340 A | 3/1995 | Lee |
| 5,397,222 A | 3/1995 | Moss et al. |
| 5,411,482 A | 5/1995 | Campbell |
| 5,415,532 A | 5/1995 | Loughnane et al. |
| 5,419,684 A | 5/1995 | Struble et al. |
| 5,423,746 A | 6/1995 | Burkett et al. |
| 5,423,759 A | 6/1995 | Campbell |
| 5,429,602 A | 7/1995 | Hauser |
| 5,431,627 A | 7/1995 | Pastrone et al. |
| 5,433,704 A | 7/1995 | Ross et al. |
| 5,433,710 A | 7/1995 | VanAntwerp et al. |
| D361,379 S | 8/1995 | Sancoff et al. |
| D361,617 S | 8/1995 | Sancoff et al. |
| 5,437,635 A | 8/1995 | Fields et al. |
| 5,437,642 A | 8/1995 | Thill et al. |
| 5,458,469 A | 10/1995 | Hauser |
| 5,458,578 A | 10/1995 | Sebesta et al. |
| 5,462,051 A | 10/1995 | Oka et al. |
| 5,462,525 A | 10/1995 | Srisathapat et al. |
| 5,466,218 A | 11/1995 | Srisathapat et al. |
| 5,472,317 A | 12/1995 | Field et al. |
| 5,472,420 A | 12/1995 | Campbell |
| 5,478,211 A | 12/1995 | Dominiak et al. |
| 5,482,446 A | 1/1996 | Williamson et al. |
| 5,485,408 A | 1/1996 | Blomquist |
| D367,527 S | 2/1996 | Marston et al. |
| D367,528 S | 2/1996 | Marston et al. |
| 5,489,265 A | 2/1996 | Montalvo et al. |
| 5,501,665 A | 3/1996 | Jhuboo et al. |
| 5,503,538 A | 4/1996 | Wiernicki et al. |
| 5,505,709 A | 4/1996 | Funderburk et al. |
| 5,507,412 A | 4/1996 | Ebert et al. |
| 5,511,951 A | 4/1996 | O'Leary |
| 5,513,957 A | 5/1996 | O'Leary |
| 5,514,103 A | 5/1996 | Srisathapat et al. |
| 5,520,638 A | 5/1996 | O'Quinn et al. |
| D371,194 S | 6/1996 | Marston et al. |
| 5,522,798 A | 6/1996 | Johnson et al. |
| 5,522,799 A | 6/1996 | Furukawa |
| 5,527,307 A | 6/1996 | Srisathapat et al. |
| 5,529,214 A | 6/1996 | Lasonde et al. |
| 5,531,680 A | 7/1996 | Dumas et al. |
| 5,531,697 A | 7/1996 | Olsen et al. |
| 5,533,981 A | 7/1996 | Mandro et al. |
| 5,545,140 A | 8/1996 | Conero et al. |
| 5,547,470 A | 8/1996 | Johnson et al. |
| 5,549,460 A | 8/1996 | O'Leary |
| 5,551,850 A | 9/1996 | Williamson et al. |
| 5,554,115 A | 9/1996 | Thomas et al. |
| 5,554,123 A | 9/1996 | Herskowitz |
| 5,562,621 A | 10/1996 | Claude et al. |
| 5,569,186 A | 10/1996 | Lord et al. |
| 5,573,502 A | 11/1996 | LeCocq et al. |
| 5,573,506 A | 11/1996 | Vasko |
| 5,578,077 A | 11/1996 | Kassatly |
| D376,848 S | 12/1996 | Zelig et al. |
| 5,584,811 A | 12/1996 | Ross et al. |
| 5,586,629 A | 12/1996 | Shoberg et al. |
| 5,588,815 A | 12/1996 | Zaleski, II |
| 5,601,420 A | 2/1997 | Warner et al. |
| 5,609,575 A | 3/1997 | Larson et al. |
| 5,620,312 A | 4/1997 | Hyman et al. |
| RE35,501 E | 5/1997 | Ross et al. |
| 5,628,619 A | 5/1997 | Wilson |
| 5,630,710 A | 5/1997 | Tune et al. |
| D380,260 S | 6/1997 | Hyman |
| 5,637,093 A | 6/1997 | Hyman et al. |
| 5,637,095 A | 6/1997 | Nason et al. |
| 5,643,212 A | 7/1997 | Coutre et al. |
| 5,647,853 A | 7/1997 | Feldmann et al. |
| 5,647,854 A | 7/1997 | Olsen et al. |
| 5,665,070 A | 9/1997 | McPhee |
| 5,669,877 A | 9/1997 | Blomquist |
| 5,673,588 A | 10/1997 | Raymond |
| 5,681,284 A | 10/1997 | Herskowitz |
| 5,681,285 A | 10/1997 | Ford et al. |
| 5,683,367 A | 11/1997 | Jordan et al. |
| 5,685,844 A | 11/1997 | Marttila |
| 5,695,464 A | 12/1997 | Viallet |
| 5,695,473 A | 12/1997 | Olsen |
| D390,654 S | 2/1998 | Alsberg et al. |
| 5,713,856 A | 2/1998 | Eggers et al. |
| 5,722,957 A | 3/1998 | Steinbach |
| 5,743,878 A | 4/1998 | Ross et al. |
| 5,745,378 A | 4/1998 | Barker et al. |
| 5,752,976 A | 5/1998 | Duffin et al. |
| 5,764,034 A | 6/1998 | Bowman et al. |
| 5,766,155 A | 6/1998 | Hyman et al. |
| 5,769,823 A | 6/1998 | Otto |
| 5,776,345 A | 7/1998 | Truitt et al. |
| 5,782,805 A | 7/1998 | Meinzer et al. |
| 5,785,681 A | 7/1998 | Indravudh |
| D397,432 S | 8/1998 | Rake et al. |
| 5,788,669 A | 8/1998 | Peterson |
| 5,791,880 A | 8/1998 | Wilson |
| 5,795,327 A | 8/1998 | Wilson et al. |
| 5,807,322 A | 9/1998 | Lindsey et al. |
| 5,807,336 A | 9/1998 | Russo et al. |
| 5,813,972 A | 9/1998 | Nazarian et al. |

| | | | | | | |
|---|---|---|---|---|---|---|
| 5,814,015 | A | 9/1998 | Gargano et al. | 6,592,551 B1 | 7/2003 | Cobb |
| 5,814,019 | A | 9/1998 | Steinbach et al. | D479,323 S | 9/2003 | Gillespie, Jr. et al. |
| 5,836,915 | A | 11/1998 | Steinbach et al. | 6,620,151 B2 | 9/2003 | Blischak et al. |
| 5,840,058 | A | 11/1998 | Ammann et al. | 6,648,861 B2 | 11/2003 | Platt et al. |
| 5,842,841 | A | 12/1998 | Danby et al. | 6,652,493 B1 | 11/2003 | Das |
| D404,813 | S | 1/1999 | Hauser | 6,656,148 B2 | 12/2003 | Das et al. |
| 5,868,710 | A | 2/1999 | Battiato et al. | 6,659,980 B2 | 12/2003 | Moberg et al. |
| 5,871,465 | A | 2/1999 | Vasko | 6,666,845 B2 | 12/2003 | Hooper et al. |
| 5,885,245 | A | 3/1999 | Lynch et al. | 6,692,241 B2 | 2/2004 | Watanabe et al. |
| D408,911 | S | 4/1999 | Moubayed et al. | 6,755,814 B2 | 6/2004 | Wieland et al. |
| 5,894,273 | A | 4/1999 | Meador et al. | 6,776,773 B2 | 8/2004 | Kiyatake et al. |
| 5,895,371 | A | 4/1999 | Levitas et al. | 6,800,069 B2 | 10/2004 | Lampropoulos et al. |
| 5,897,530 | A | 4/1999 | Jackson | 6,805,687 B2 | 10/2004 | Dextradeur et al. |
| 5,904,668 | A | 5/1999 | Hyman et al. | 6,827,702 B2 | 12/2004 | Lebel et al. |
| 5,908,414 | A | 6/1999 | Otto et al. | 6,854,620 B2 | 2/2005 | Ramey |
| 5,935,099 | A | 8/1999 | Peterson et al. | 6,945,954 B2 | 9/2005 | Hochman et al. |
| 5,935,106 | A | 8/1999 | Olsen | 6,999,854 B2 | 2/2006 | Roth |
| 5,943,633 | A | 8/1999 | Wilson et al. | 7,008,403 B1 | 3/2006 | Mallett |
| 5,951,510 | A | 9/1999 | Barak | 7,018,361 B2 | 3/2006 | Gillespie, Jr. et al. |
| 5,954,696 | A | 9/1999 | Ryan | 7,022,107 B1 | 4/2006 | Christensen et al. |
| 5,954,697 | A | 9/1999 | Srisathapat et al. | 7,025,226 B2 | 4/2006 | Ramey |
| 5,957,890 | A | 9/1999 | Mann et al. | 7,029,455 B2 | 4/2006 | Flaherty |
| 5,988,983 | A * | 11/1999 | Furusawa ..................... 417/43 | 7,092,796 B2 | 8/2006 | Vanderveen |
| 5,993,420 | A | 11/1999 | Hyman et al. | 7,182,750 B2 | 2/2007 | Lampropoulos et al. |
| 6,004,020 | A | 12/1999 | Bartur | 7,193,521 B2 | 3/2007 | Moberg et al. |
| 6,013,057 | A | 1/2000 | Danby et al. | 7,232,423 B2 | 6/2007 | Mernoe |
| D420,737 | S | 2/2000 | Kivlehan | 7,236,936 B2 | 6/2007 | White et al. |
| 6,024,539 | A | 2/2000 | Blomquist | 7,255,683 B2 | 8/2007 | Vanderveen et al. |
| 6,078,273 | A | 6/2000 | Hutchins et al. | 7,306,578 B2 | 12/2007 | Gray et al. |
| 6,083,201 | A | 7/2000 | Skinkle | 7,322,961 B2 | 1/2008 | Forrest |
| D430,288 | S | 8/2000 | Mason et al. | 7,338,464 B2 | 3/2008 | Blischak et al. |
| D430,289 | S | 8/2000 | Mason et al. | 7,341,581 B2 | 3/2008 | Mallett |
| 6,095,757 | A | 8/2000 | Frezza | 7,347,837 B2 | 3/2008 | Azzolini |
| 6,106,498 | A | 8/2000 | Friedli et al. | 7,351,226 B1 | 4/2008 | Herskowitz |
| 6,110,152 | A | 8/2000 | Kovelman | 7,356,382 B2 | 4/2008 | Vanderveen |
| 6,123,524 | A | 9/2000 | Danby et al. | 7,374,556 B2 | 5/2008 | Mallett |
| 6,129,517 | A | 10/2000 | Danby et al. | D574,016 S | 7/2008 | Yodfat et al. |
| 6,135,949 | A | 10/2000 | Russo et al. | D577,118 S | 9/2008 | Yodfat et al. |
| 6,139,748 | A | 10/2000 | Ericson et al. | 7,471,994 B2 | 12/2008 | Ford et al. |
| D434,142 | S | 11/2000 | Cheney, II et al. | 7,534,226 B2 | 5/2009 | Mernoe et al. |
| 6,145,695 | A | 11/2000 | Garrigues | 7,559,926 B1 | 7/2009 | Blischak |
| 6,173,198 | B1 | 1/2001 | Schulze et al. | 7,569,030 B2 | 8/2009 | Lebel et al. |
| 6,195,887 | B1 | 3/2001 | Danby et al. | 7,601,148 B2 | 10/2009 | Keller |
| 6,203,528 | B1 | 3/2001 | Deckert et al. | 7,608,060 B2 | 10/2009 | Gillespie, Jr. et al. |
| 6,213,723 | B1 | 4/2001 | Danby et al. | 7,611,498 B2 | 11/2009 | Hasler |
| 6,213,738 | B1 | 4/2001 | Danby et al. | 7,621,893 B2 | 11/2009 | Moberg et al. |
| 6,231,560 | B1 | 5/2001 | Bui et al. | 7,632,249 B2 | 12/2009 | Momeni et al. |
| 6,269,340 | B1 | 7/2001 | Ford et al. | 7,637,892 B2 | 12/2009 | Steinbach et al. |
| D446,854 | S | 8/2001 | Cheney, II et al. | 7,647,237 B2 | 1/2010 | Malave et al. |
| 6,270,478 | B1 | 8/2001 | Mernøe | D612,484 S | 3/2010 | Yodfat et al. |
| 6,280,416 | B1 | 8/2001 | Van Antwerp et al. | D614,587 S | 4/2010 | Yodfat et al. |
| D447,558 | S | 9/2001 | Cartledge et al. | 7,708,717 B2 | 5/2010 | Estes et al. |
| 6,297,795 | B1 | 10/2001 | Kato et al. | 7,717,903 B2 | 5/2010 | Estes et al. |
| 6,305,908 | B1 | 10/2001 | Hermann et al. | 7,725,272 B2 | 5/2010 | Ginggen et al. |
| D453,830 | S | 2/2002 | McDowell et al. | 7,743,975 B2 | 6/2010 | Miller |
| 6,347,553 | B1 | 2/2002 | Morris et al. | 7,758,552 B2 | 7/2010 | Zoltan et al. |
| 6,348,043 | B1 | 2/2002 | Hagen et al. | 7,766,863 B2 | 8/2010 | Gillespie, Jr. et al. |
| 6,348,952 | B1 | 2/2002 | Jeong | 7,766,873 B2 | 8/2010 | Moberg et al. |
| 6,358,225 | B1 | 3/2002 | Butterfield | 7,776,029 B2 | 8/2010 | Whitehurst et al. |
| D457,949 | S | 5/2002 | Krug et al. | 7,776,030 B2 | 8/2010 | Estes et al. |
| 6,398,760 | B1 | 6/2002 | Danby | 7,789,859 B2 | 9/2010 | Estes et al. |
| 6,413,239 | B1 | 7/2002 | Burns et al. | 7,794,426 B2 | 9/2010 | Briones et al. |
| 6,423,035 | B1 | 7/2002 | Das et al. | 7,794,427 B2 | 9/2010 | Estes et al. |
| D461,241 | S | 8/2002 | Moberg et al. | 7,794,428 B2 | 9/2010 | Estes et al. |
| D461,891 | S | 8/2002 | Moberg | 7,803,134 B2 | 9/2010 | Sharifi et al. |
| D462,121 | S | 8/2002 | Cartledge et al. | 7,833,196 B2 | 11/2010 | Estes et al. |
| 6,458,102 | B1 | 10/2002 | Mann et al. | 7,837,651 B2 | 11/2010 | Bishop et al. |
| 6,471,436 | B1 | 10/2002 | Gjata et al. | 7,850,641 B2 | 12/2010 | Lebel et al. |
| 6,475,180 | B2 | 11/2002 | Peterson et al. | 2001/0031944 A1 | 10/2001 | Peterson et al. |
| 6,485,465 | B2 | 11/2002 | Moberg et al. | 2001/0034502 A1 | 10/2001 | Moberg et al. |
| 6,489,896 | B1 | 12/2002 | Platt et al. | 2002/0004645 A1 | 1/2002 | Carlisle et al. |
| 6,500,151 | B1 | 12/2002 | Cobb et al. | 2002/0128606 A1 | 9/2002 | Cowan et al. |
| 6,519,569 | B1 | 2/2003 | White et al. | 2002/0165491 A1 | 11/2002 | Reilly |
| 6,544,229 | B1 | 4/2003 | Danby et al. | 2003/0009133 A1 | 1/2003 | Ramey |
| 6,554,822 | B1 | 4/2003 | Holschneider et al. | 2003/0060754 A1 | 3/2003 | Reilly et al. |
| D474,837 | S | 5/2003 | Gillespie, Jr. et al. | 2003/0060768 A1 | 3/2003 | Kiyatake et al. |
| D475,454 | S | 6/2003 | Gillespie, Jr. et al. | 2003/0065287 A1 | 4/2003 | Spohn et al. |
| 6,572,604 | B1 | 6/2003 | Platt et al. | 2003/0073954 A1 | 4/2003 | Moberg et al. |
| 6,585,675 | B1 | 7/2003 | O'Mahony et al. | 2003/0078534 A1 | 4/2003 | Hochman et al. |

| | | | |
|---|---|---|---|
| 2003/0097092 A1 | 5/2003 | Flaherty | |
| 2003/0149402 A1 | 8/2003 | Gerlach et al. | |
| 2010/0106082 A1 | 4/2010 | Zhou | |

FOREIGN PATENT DOCUMENTS

| | | | |
|---|---|---|---|
| EP | 0426273 A1 | 2/1989 | |
| EP | 0374618 | 6/1990 | |
| EP | 0447985 | 9/1991 | |
| EP | 0522527 | 1/1993 | |
| EP | 0560270 | 9/1993 | |
| EP | 0567944 | 11/1993 | |
| EP | 0567945 | 11/1993 | |
| EP | 0567946 | 11/1993 | |
| EP | 0567962 | 11/1993 | |
| EP | 0800840 A2 | 10/1997 | |
| EP | 0881388 | 12/1998 | |
| EP | 1834658 | 9/2008 | |
| EP | 2062605 | 5/2009 | |
| GB | 2190145 | 11/1987 | |
| GB | 2208897 | 4/1989 | |
| GB | 2336510 | 10/1999 | |
| WO | WO84/04685 | 12/1984 | |
| WO | WO92/03656 | 3/1992 | |
| WO | WO93/05829 | 4/1993 | |
| WO | WO95/17913 | 7/1995 | |
| WO | 96/18038 | 6/1996 | |
| WO | WO00/42911 | 7/2000 | |
| WO | WO00/48112 | 8/2000 | |
| WO | WO00/68766 | 11/2000 | |

OTHER PUBLICATIONS

International Search Report for International Application No. PCT/US 02/36964 of Applicant Baxter International Inc., Dated 2003.
International Search Report for International Application No. PCT/US2010/026945 dated Aug. 9, 2010.
Written Opinion for International Application No. PCT/US2010/026945 dated Aug. 9, 2010.
International Preliminary Report for International Patent Application No. PCT/US2010/026945 dated Jun. 22, 2011.

* cited by examiner

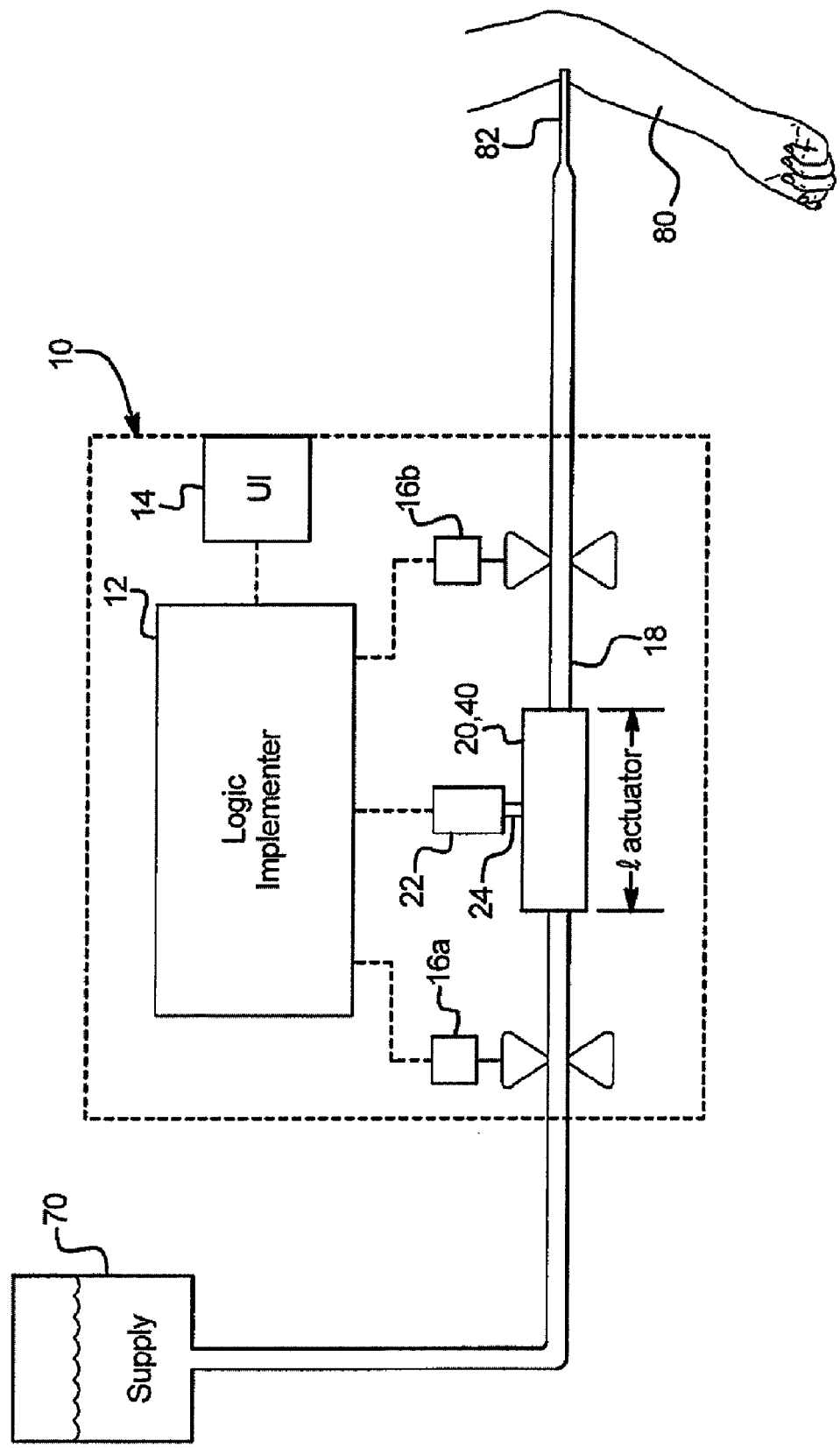

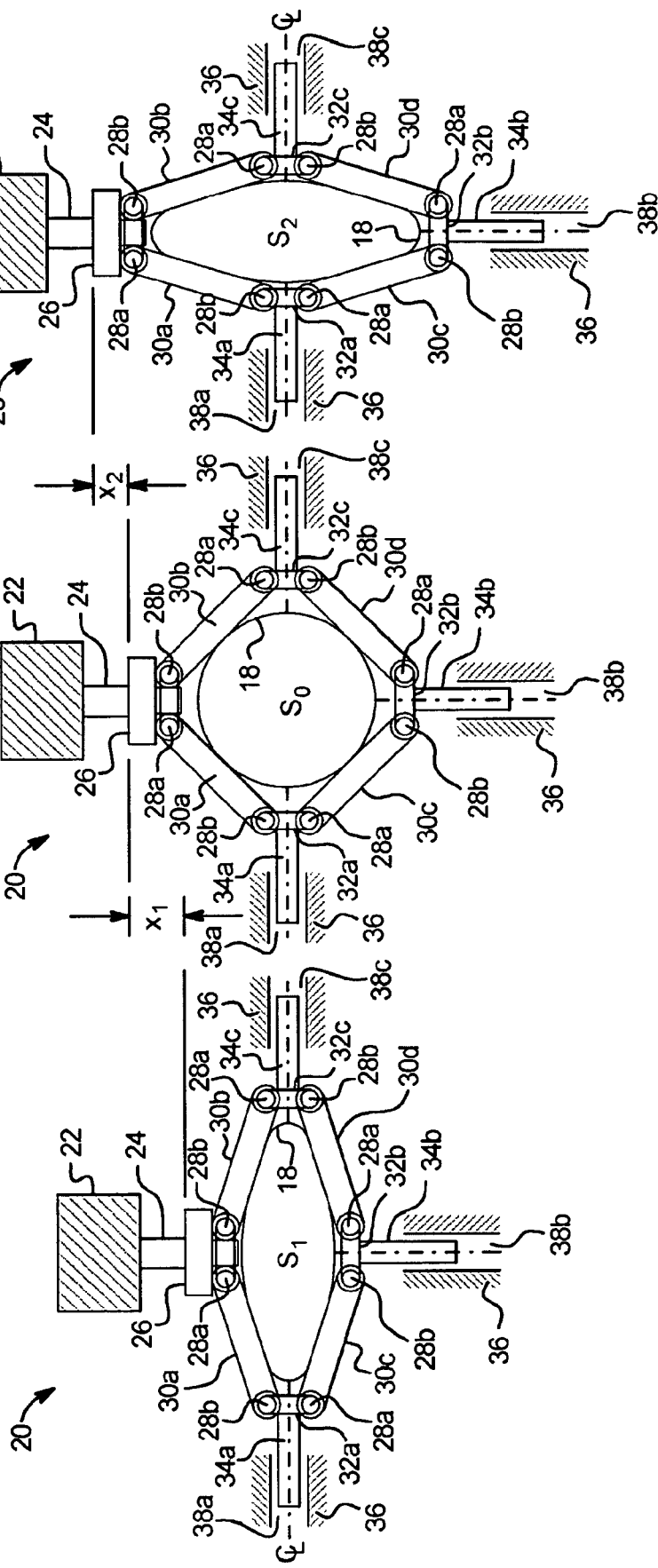

INFUSION PUMP ACTUATORS, SYSTEM AND METHOD FOR CONTROLLING MEDICAL FLUID FLOWRATE

BACKGROUND

The present disclosure relates to medical devices and more particularly to infusion pumps.

Infusion pumps or tubing pumps are used commonly to inject drugs or medicaments into a patient. Tubing pumps are relatively simple compared to diaphragm pumps. Also, tubing pumps operate directly with tubing and do not require operation with a disposable pumping cassette or flexible membrane. The disposable cost of a treatment is accordingly reduced. Moreover, the tubing is relatively simple to sterilize and keep sterile.

One problem with tubing pumps is accuracy. Volumetric control of peristaltic tubing pumps usually consists of counting a number of times that the pump roller is revolved against a tube loaded against a peristaltic pump race and assuming a volume for each revolution. The assumed volume is based on a internal volume of the tube that is contacted by the pump roller. One problem with the assumption is when the tube does not de-compress to its initial de-compressed shape after the pump roller has passed. This problem generally worsens over time as the pump tubing material becomes less and less resilient due to the persistent compression and decompression of the pump tubing.

A need accordingly exists to provide an infusion or tubing type medical fluid pump having increased accuracy.

SUMMARY

The infusion pumps of the present disclosure are used to administer liquid drugs or medicaments to patients. The pumps supply a liquid from a source of the drug or medicament and deliver the drug to the patient via a catheter or other injection device. The infusion pump controls the manner in which the liquid drug is infused to the patient. The pump has various modes of infusion, such as: (i) a continuous mode in which the pump delivers a single volume at a single rate; (ii) an auto-ramp mode in which the pump delivers the liquid drug at a rate that gradually increases to a threshold rate, remains at the threshold rate for a period of time, and then gradually decreases; (iii) an intermittent mode in which the pump delivers discrete liquid volumes spaced over relatively long periods of time, such as a liquid volume every three hours; (iv) a custom mode in which the pump can be programmed to deliver a unique infusion rate at discrete time periods; and (v) a pain controlled analgesic ("PCA") mode during which the pump periodically infuses boluses of an analgesic in response to requests by the patient.

The present disclosure provides an infusion pump having a pump actuator that helps the tubing to return to a perfect or near perfect circular shape upon a pump-in stroke to improve overall efficiency and accuracy of the pump. Also, the tubing shape change during pumping can be theoretically modeled, therefore, the pumping accuracy can be controlled based on a theoretical model within a pumping cycle, which also improves pumping accuracy. Pumping accuracy can be even more critical when very low flowrates are required. In other pumps, the resiliency of the tubing is relied upon to bring the tubing back to its circular shape upon decompression. Sometimes, however, especially after repeated use, the tubing only partially returns to its original circular shape. This results in inaccuracy and incomplete pump fills. Further, some pump actuators place a twisting or torque on the tube, which can permanently twist the tube over time.

The present actuators operate with an infusion pump that includes upstream and downstream valves. The upstream valve is opened and the downstream valve is closed upon a pump-in stroke. Here, the pump actuator is actuated so as to actively bring the tubing back to its original opened and perfectly (or near perfectly) circular shape, and does so without placing a twisting or torque force on the tubing. This allows the controller or logic implementer of the pump to accurately assume that the pump-fill volume is equal to the inner diameter area of the tubing multiplied by a length of the section of the tubing that is compressed and decompressed.

Upon a pump-out stroke, the valve state is switched, such that the inlet valve or occluder is, clamped, while the outlet valve or occluder is opened. The pump actuator compresses the tubing to push a volume of fluid to the patient. The volume of fluid remaining in the tubing section at the end of the pump-out stroke (which is optimally zero) is subtracted from the volume of fluid sucked in at the end of the pump-in stroke is the amount of fluid delivered to the patient for that stroke. The total number of strokes multiplied by that volume provides the total volume of fluid delivered to the patient during a treatment or portion of treatment. The frequency at which pump-in and pump-out strokes are sequenced establishes the rate at which medical fluid is delivered to the patient. The pump actuators of the present disclosure are configured to virtually completely compress the tubing, such that the end of stroke pump-out volume is zero or virtually zero.

In one primary embodiment, the pump actuator includes four hinge members, which are hinged together via mounting links. One of the mounting links is connected to an output shaft of a linear actuator. The remaining three mounting links each include a slide, which fits slidingly into slots formed in the body of the infusion pump. Such arrangement allows the pump actuator to compress the tubing by either pulling the output shaft in or pushing the output shaft out. The output shaft is then either pushed out or pulled in, respectively, to bring the tubing back to its original, round shape. In both cases, the hinge members guide the tubing during both the pump-in and pump-out strokes, so as not to rely upon the elasticity of the tubing.

In this first embodiment, the tubing is fitted through the four member hinged assembly, such that the tube is subjected to compressive but not to twisting or torque-like forces that can twist the tubing. Position sensors can be placed within the machine body, for example, in slots that receive the slides connected to the links, so as to sense the slides to detect pump-fill and pump-expel end-of-stroke positions. The end of stroke sensors can be proximity sensors that inductively or capacitively sense one of the slides when either a pump-out or pump-in end-of-stroke position is reached.

In a second primary embodiment, the pump actuator again includes four hinge members, which are hinged together. Here, the hinge members are hinged together directly, eliminating the connecting links and associated slides of the first primary embodiment. The first primary embodiment includes eight hinge points (two per link), while the second primary embodiment includes four hinge points. In the second primary embodiment, instead of allowing slide members to slide within slots formed in the infusion pump body, a hinge point (located opposite of the hinge point connected to the linear actuator output shaft) is fixed via bearings to the machine body. The two remaining hinge points move freely. The linear actuator moves the hinge members from a diamond shape to a compressed shape at the machine body and then pulls the hinge members back to the diamond shape. The tubing is accordingly compressed, virtually completely, and then pulled back to a virtually perfect circular shape, improving pump efficiency and accuracy. Again, the tubing is fitted through the diamond shaped hinge member structure, such that forces are applied compressively, e.g., in the direction of the output shaft; and not in a tangential torque-like manner, which can twist the tubing. End-of-stroke sensors are placed in appropriate positions to sense when the pump actuator is either at the pump-in end-of-stroke position or pump-out end-of-stroke position.

In both the first and second primary embodiments, the cross-sectional area of the tubing is known for any position of a linear actuator that drives the pump actuator. The position of the linear actuator is known at any given point in time, e.g., via encoder or sensor feedback. A first relationship is formed based on the fact that the hinge members of the pump actuator are rigid and constant. A second relationship is formed based on the fact that the tubing diameter in an uncompressed position is known and constant. A third relationship is formed based on the assumption that the tubing will expand as much as possible within the hinged members structures as the structures are collapsed for pumping. The three relationships allow three variables needed for cross-sectional area at any given distance x to be solved. Solving for instantaneous cross-sectional area multiplied by the pump actuator length $l_{actuator}$, allows instantaneous volume to be solved. Differentiating flowrate over time yields flowrate and thus the control of flowrate via a linear actuator motion profile. The profile can be developed such that the flowrate is constant, which is desirable.

It is accordingly an advantage of the present disclosure to provide an improved medical infusion pump.

It is another advantage of the present disclosure to provide an infusion pump having a pump actuator that aids the tubing in both pump-in and pump-out strokes.

It is yet another advantage of the present disclosure to provide an infusion pump having a pump actuator, which has increased efficiency and accuracy.

Still further, it is an advantage of the present disclosure to provide an infusion pump having a pump actuator, which assists in decompressing the pump tubing without providing a torsional or twisting force on the tubing.

Moreover, it is an advantage of the present disclosure to provide a system and method for controlling infusion pump flowrate.

Additional features and advantages are described herein, and will be apparent from the following Detailed Description and the figures.

BRIEF DESCRIPTION OF THE FIGURES

FIG. 1 is a schematic view of a valve and medical fluid flow arrangement for the medical fluid pump actuators and associated infusion pumps of the present disclosure.

FIGS. 2A to 2C are side elevation views illustrating the operation of one embodiment of the infusion pump actuator of the infusion pump of the present disclosure, which includes multiple hinge members and connecting lineages.

DETAILED DESCRIPTION

Figure 4A:
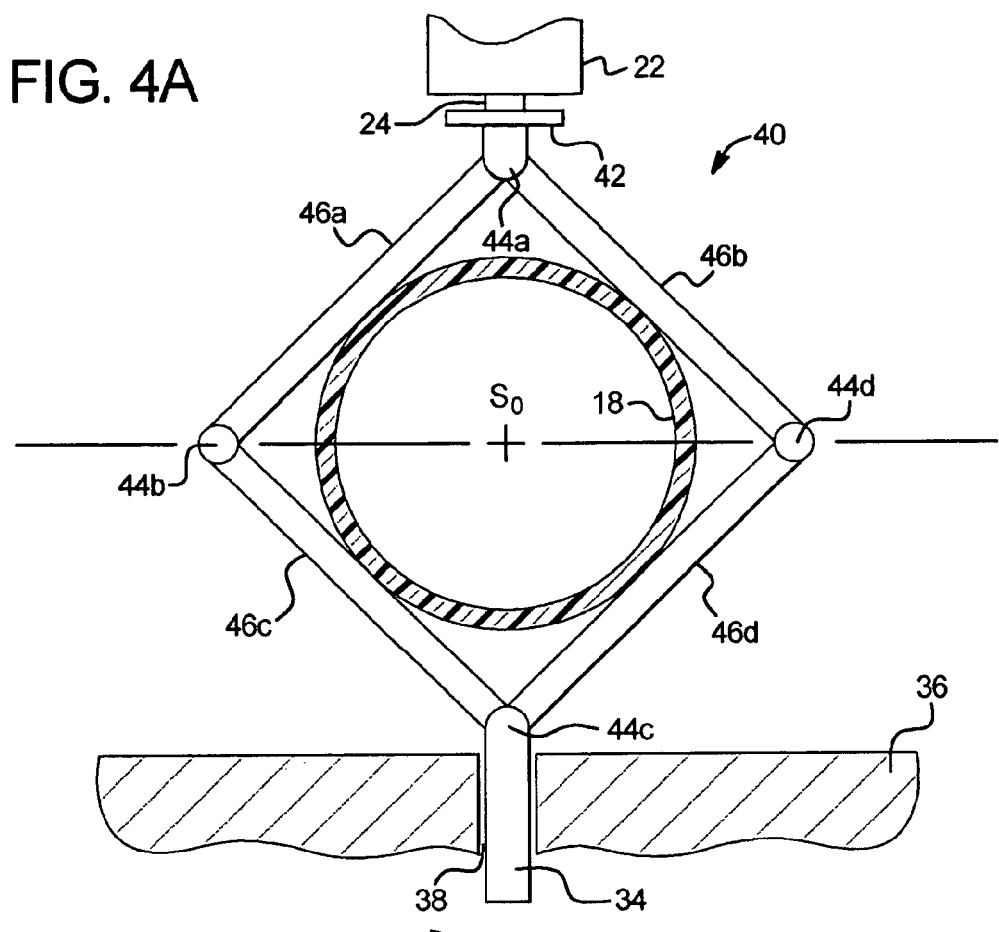
FIGS. 4A and 4B are side elevational views illustrating the operation of another embodiment of the infusion pump actuator of the present disclosure, which includes multiple directly hinged members.
Figure 4B:
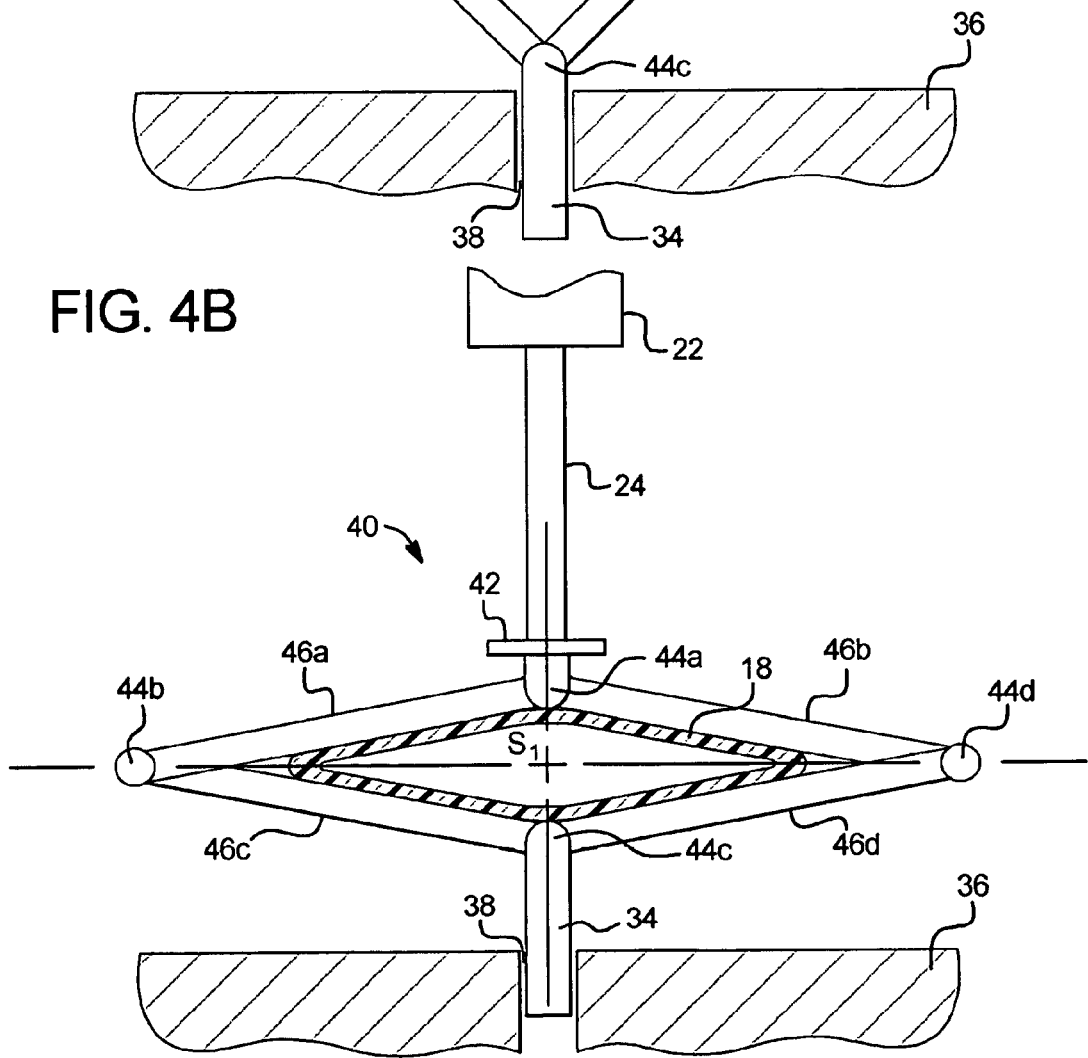
Figure 5:
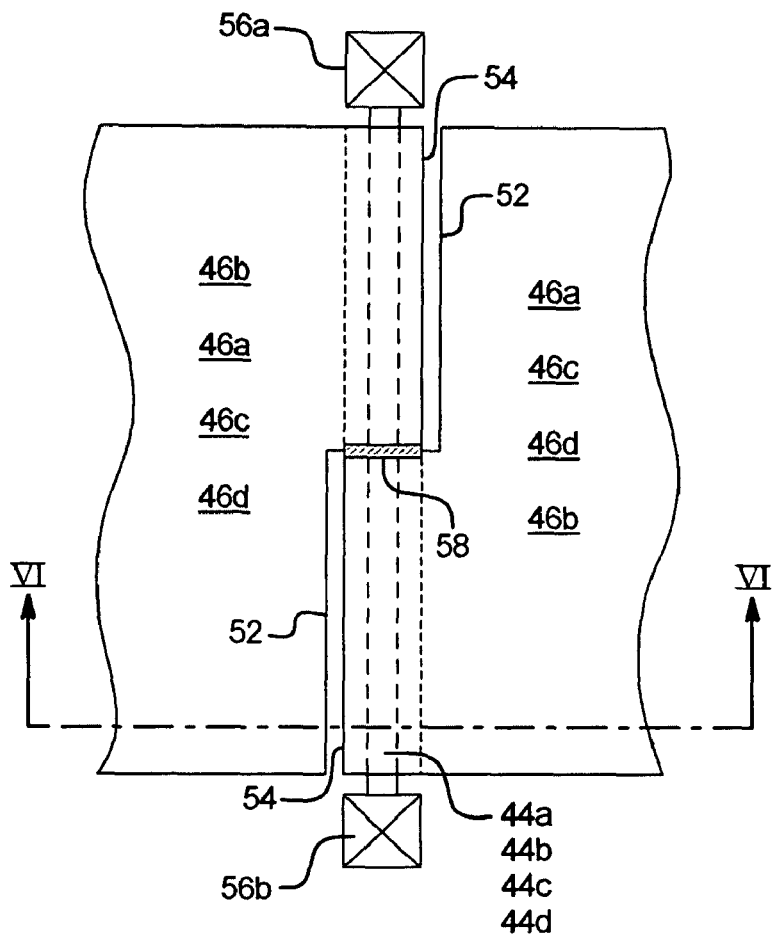
FIG. 5 is a top plan view of one embodiment for hinging the members of the pump actuators of FIGS. 4A and 4B of the infusion pump of the present disclosure.
Figure 6:
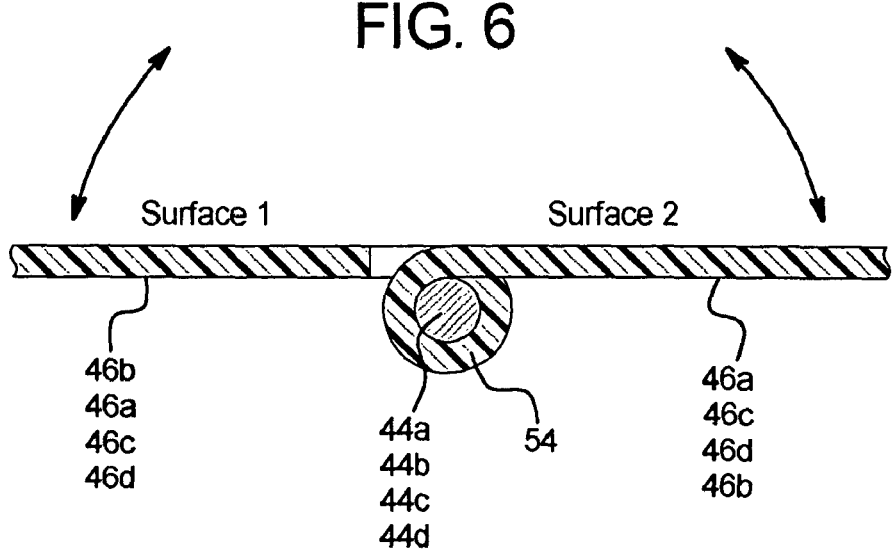
FIG. 6 is a sectioned elevation view taken along line VI-VI of FIG. 5.

FIGS. 2A to 2C show one preferred embodiment, which has the advantages of: (i) controlling tube shape and (ii) allowing for an area/volume within the pumped tubing segment at a given point of a pump stroke to be modeled (allowing fluid flowrate to be calculated). FIGS. 4A and 4B show another embodiment that also has the advantages of: (i) controlling tube shape and (ii) allowing for an area/volume within the pumped tubing segment at a given point of a pump stroke to be modeled. FIGS. 5 and 6 illustrate a suitable hinge arrangement for the embodiment of FIGS. 4A and 4B.

Referring now to FIG. 1, a schematic illustration of infusion pump 10 is illustrated. Pump 10 pumps a drug or medicament from a supply 70, through a tube 18, to a patient 80, via a patient catheter or cannula 82. Tube 18 as illustrated is loaded into infusion pump 10, so that the pump can pull fluid from supply 70 and move the fluid in a controlled manner through tube 18, catheter or cannula 82 to patient 80. Infusion pump 10 includes a logic implementer 12. Logic implementer 12 includes one or more processor, such as supervisory processor that controls one or more delegate processor, which in turn controls various aspects of infusion pump 10. Logic implementer 12 can, for example, employ a safety or monitoring processor, which ensures that the supervisory processor and delegate control processors are operating properly. The processors operate with one or more memory, which is also part of logic implementer 12. As shown, logic implementer 12 operates with or controls a user interface 14. The user interface 14 displays information to the patient or operator and also allows the patient or operator to enter information from the user interface into logic implementer 12. To that end, user interface 14 can operate with a touch screen overlay or with one or more electromechanical input device, such as a membrane switch.

User interface 14 enables the operator to command logic implementer 12 to control infusion pump 10 so as to run: (i) a continuous mode in which pump 10 delivers liquid via tubing 18 to achieve a desired volume at a single flow rate; (ii) an auto-ramp mode in which infusion pump 10 delivers liquid from supply 70 at a rate that gradually increases to a threshold, remains at the threshold rate for a prescribed time, and then gradually decreases; (iii) an intermediate mode in which infusion pump 10 delivers discrete liquid volumes spaced over relatively long periods of time, such as a bolus or volume every three hours; (iv) a custom mode in which infusion pump 10 delivers a unique infusion rate at different time intervals; and (v) a pain-controlled analgesic ("PCA") mode during which patient 80 presses a button causing infusion pump 10 to periodically infuse a bolus of analgesic into the patient.

To provide the various modes of delivery, logic implementer 12 operates an upstream valve or occluder 16a, a downstream valve or occluder 16b and a pump actuator 20 or 40 described in detail below. To pump a known volume of drug or medicament, logic implementer causes valve or occluder 16a to pinch or compress tubing 18 upstream of pump actuator 20 or 40. Logic implementer 12 also causes valve or occluder 16b to open and at the same time or slightly thereafter causes one of the pump actuators 20 or 40 to compress tubing 18, forcing a known volume of fluid down tubing towards catheter or cannula 82 and patient 80. The known volume of fluid is set by a length $l_{actuator}$ of the clamping portion of the pump actuator 20 or 40 multiplied by an internal area of tubing 18.

After the drug or medicament volume is delivered to patient 80, logic implementer 12 causes downstream valve or occluder 16b to close and simultaneously or slightly thereafter opens valve 16a, allowing medical fluid from supply 70 to be in fluid communication with the inlet of pump actuator 20 or 40. Logic implementer 12 causes the pump actuator to decompress tubing 18, creating a vacuum, which draws the drug or medicament into tubing 18 within the length L of the clamping portion of the pump actuator 20 or 40.

Logic implementer 12 repeats the above-described valve sequencing and pump actuation until a desired total amount of medical fluid is delivered via cannula or catheter 82 to patient 80. The total volume is equal to the individual pump volumes multiplied by the number of sequences. The rate at which valves 16a and 16b are switched in combination with the pump actuation sets the rate at which the drug or medicament is delivered to patient 80.

Referring now to FIGS. 2A to 2C, one embodiment of the pump actuator described in FIG. 1 for infusion pump 10 is illustrated by pump actuator 20. Pump actuator 20, like actuator 40, helps to decompress tubing 18 to a full and complete circular shape on the pump-in stroke, increasing the efficiency and accuracy of the pump actuator and resulting infusion pump 10. That is, tubing 18 is controlled to change shape in both the pump-out and pump-in strokes, so as not to rely on the elasticity or resiliency of tubing 18 for the pump-in stroke. Tubing 18 can be made of polyvinylchloride ("PVC") or suitable non-PVC material, such as silicone. While these materials have resiliency, the tubing may not return to its full shape if left to do so on its own. This problem worsens over time and use. Moreover, tubing 18 in pump actuator 20 is not twisted, rather, it is compressed via normal forces, such that the tubing 18 section within the pump actuator will not twist over time.

Pump actuator 20 in FIGS. 2A to 2C includes a linear actuator 22 operable with an output shaft 24, which is either retracted into linear actuator 22 or pushed out of linear actuator 22 ($l_{actuator}$ is into or out of the page). In one embodiment, the linear actuator includes a motor, such as a stepper motor or DC brushed or brushless motor, which is coupled to a lead screw (not shown). Output shaft 24 is directly or indirectly threaded onto the lead screw and traverses back and forth depending on which direction the stepper or DC motor is rotated.

Output shaft 24 is in turn connected to a motor link 26. Motor link 26 includes first and second hinge pins 28a and 28b, which are inserted into opened, circular ends of hinge members 30a and 30b, respectively. Pump actuator 20 additionally includes slide links 32a to 32c, which each include first and second hinge pins 28a and 28b. Slide links 32a to 32c each also include a slide 34a to 34c, respectively, which is slidingly received by a slot in housing fixture or body 36 of infusion pump 10. Slide links 32a and 32c include a hinge pin 28b and 28a, respectively, which connects hingedly with an open circular end located at the opposing ends of hinge members 30a and 30b. Hinge pins 28a and 28b of slide links 32a to 32c mount to a first open circular end of hinge members 30c and 30d, respectively. Slide link 32b likewise includes a hinge pin 28b and a hinge 28a, which connect hingedly and respectively to the second or lower open circular ends of members 30c and 30d, completing the closed clamping structure of pump actuator 20. Shaft 24 and slides 34a to 34c maintain members 30a to 30d, motor link 26 and associated slide links 32a to 32c in a fixed but openable and closeable state.

Motor link 26 and slide links 32a to 32c (including slides 34a to 34c, members 30a to 30d and all associated hinge pins 28a and 28b can be made of metal, such as steel, stainless steel or aluminum, or a hard plastic, such as polycarbonate). Members 30a to 30d, links 26 and 32a to 32c and associated hinge pins 28a and 28b have a depth into or out of the page showing FIGS. 2A to 2C, which is at least substantially equal to actuator length $l_{actuator}$ shown in FIG. 1. Slides 34a to 34d can also have such a depth or be a series of pegs or plates. In a preferred embodiment, the materials of slides 34a to 34c and the surface of restraint 36 of infusion pump 10 are made so as to limit an amount of friction between restraints 36 and slides 34a to 34c.

FIG. 2A shows pump actuator 20 with tube 18 fully extended or inflated. This is the position of the pump actuator when it has just pulled a volume of drug or medicament into the section of tubing corresponding to the actuator length $l_{actuator}$ of hinge members 30a to 30d, etc.

FIG. 2B shows that linear actuator 22 can push output shaft 24 outward to compress tubing 18. Alternatively, linear actuator 22 can pull output shaft 24 inward to compress tubing 18 as shown in FIG. 2C. FIGS. 2B and 2C show tubing 18 partially compressed. It is contemplated that output shafts 24 move further in the outward direction in FIG. 2B and in the inward direction of FIG. 2C, such that tubing 18 is pressed at least substantially flat to obtain the maximum amount of delivery per stroke and to attempt to have the tubing section have as close to an inner volume of zero as possible for accuracy and efficiency purposes. That is, in one embodiment logic implementer 12 assumes that the volume of liquid remaining in section $l_{actuator}$ of tubing 18 is zero at the end of the pump-out stroke. Logic implementer 12 also assumes that the section $l_{actuator}$ of tubing 18 is an exact circle as shown in FIG. 2A at the end of the pump-in stroke. The members and links of pump actuator 20 help to ensure that these assumptions are made to be as correct as possible.

It is contemplated to place sensors, such as inductive or capacitive proximity sensors within the slots 38a to 38c defined by restraining walls 36 of infusion pump 10, so as to sense an end of a respective slide 34a to 34c to detect an end-of-stroke for pump actuator 20. For example, a first sensor can be placed in slide slot 38a in FIG. 2B so as to sense slide 34a when members 30a to 30d have fully compressed tubing 18. At the moment of sensing slide 34a, the sensor sends a signal to logic implementer 12, which stops any further outward movement of output shaft 24 from linear actuator 20. Alternatively, the sensor, such as a proximity sensor, is placed in slot 38b to sense the end of slide 34b when tubing 18 is fully compressed in FIG. 2C. If tubing compression is performed as shown in FIG. 2B, the end-of-stroke sensor for filling pump tube 18 is placed in slide slot 38b of FIG. 2A to sense slide 34b when it is pushed outward to the point at which tubing 18 becomes a perfect circle. On the other hand, if compression is done as shown in FIG. 2C, the sensor is placed in either slots 38a or 38c of FIG. 2A to determine when the pump-in stroke is completed.

In an alternative embodiment, an electrical switch contact is made via slides 34a to 34c in a similar manner as above with the sensors to indicate an end of the pump-out or pump-in stroke. The closing of the contact is sensed at logic implementer 12, which then stops any further actuation of actuator 22 for that stroke. In a further alternative embodiment, hard stops are placed within slide slots 38a to 38c, which stop slides 34a to 34c and thus members 30a to 30d and associated links at the end-of-stroke positions. Here, motor current draw increases as the motor tries to continue to turn. Logic implementer 12 senses the increase in motor current draw immediately and determines that pump actuator 20 is at the end of a pump-in or pump-out stroke.

In still a further alternative embodiment, if the motor is an electric rotating motor, the motor can be fitted with an encoder that tells logic implementer 12 how many revolutions (or sub-revolutions) the motor has made, so that the logic implementer can determine how far actuator 24 and associated members 30a to 30d links 32a to 32d have moved. A sensor(s) can be provided here to set a "home" position(s), which resets the encoder to begin a count for the pump-in and pump-out strokes.

Figure 3A:
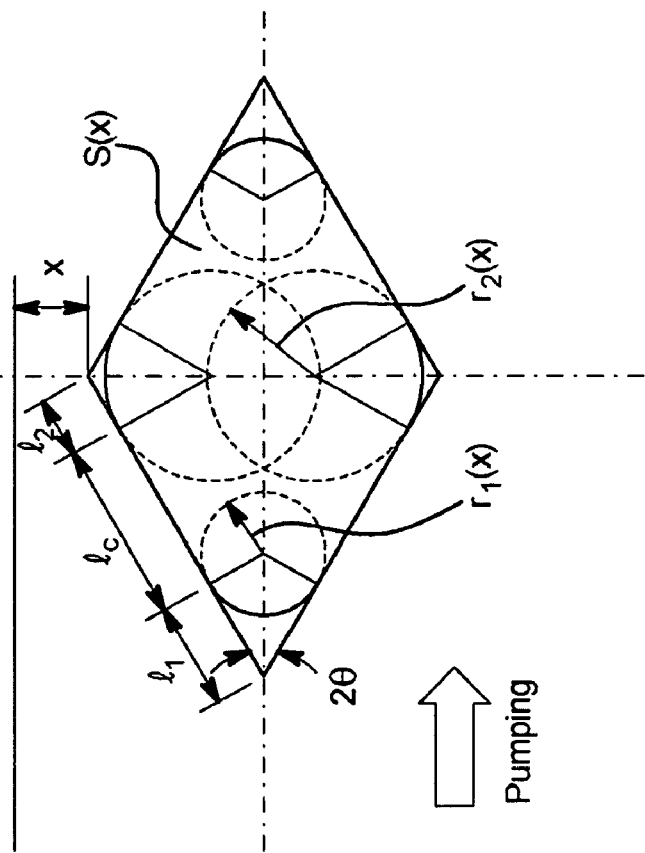
FIGS. 3A and 3B illustrate flow accuracy modeling for the infusion pump actuator of FIGS. 2A to 2C.
Figure 3B:
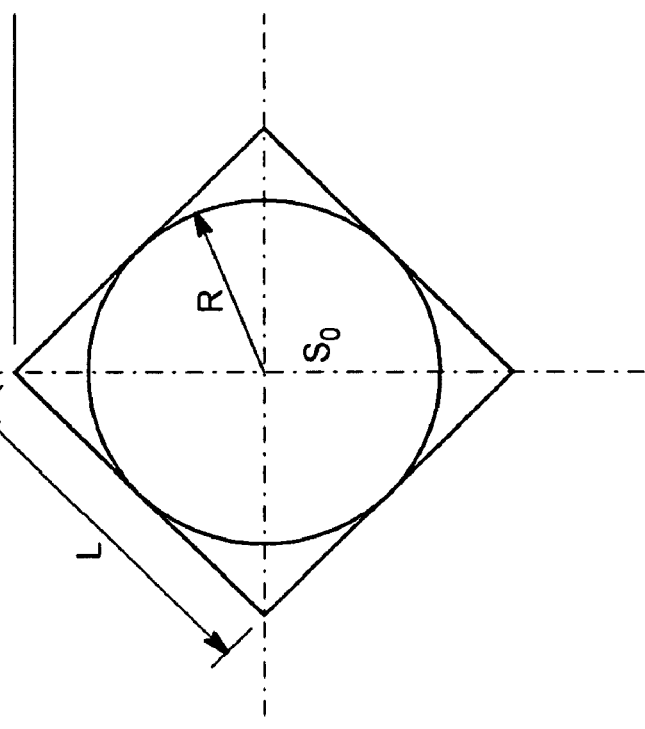

Referring now to FIGS. 3A and 3B, pump actuator 20 is modeled so as to form a relationship between a distance x that output shaft 24 and motor link 26 are moved versus an angle theta "θ", which is the angle between any of members 30a to 30d and the horizontal center line $C_L$ shown in FIGS. 2A to 2C, 3A and 3B. In FIG. 3A, each of members 30a to 30d has a length L. lc is the contact length between tubing 18 and interior surface of members 30a to 30d, relative to the actuator movement distance x of that output shaft 24 and motor link 26.

Tubing 18 has an outer radius R, which in FIG. 3A leads to an initial outer cross-sectional area $S_0$ equal to $2\pi R$. FIG. 3B shows that as tubing 18 is compressed due to the movement x of shaft 24/link 26, angle θ has changed from 45° to a lesser angle θ(x). $r_1(x)$ and $r_2(x)$ are the radii of the tangent curves at four contacting corners, that is, the break points between where tubing 18 is contacted by members 30a to 30d and where the tubing is not contacted by members 30a to 30d for a given distance of travel x. FIG. 3B shows that the circular outside cross-sectional area $S_0$ has changed to $S(x)$, which is the outer cross-sectional area of tubing 18 for any movement x of shaft 24/link 26. Note that the change in outer cross-sectional area $(|S(x)-S(0)|$ less a constant cross-sectional area $S_{thickness}$ for the area of the thickness of the tubing) times the length of pump actuator 20, $l_{actuator}$, equals the fluid volume pumped per the movement x. The instantaneous flow rate at the time t from $t_0$ that shaft 24/link 26 has traveled x is thus equal to the flow volume difference per time or $(|V(x)-V(0)|)/(t-t_0)$.

The outer cross-sectional area $S(x)$ is thought of to include the summation of three sub-areas: (i) an inner (main) sub-area bounded by four contact lengths lc's, two wedge circumferences defined by $r_2(x)$ and four radii $r_1(x)$'s; plus (ii) two outer (end) sub-areas, which are a function of $r_1(x)$ and θ(x).

(i) Knowing or measuring x; (ii) assuming (a) that length L does not change (which is correct because members 30a to 30d are rigid) and (b) that the non-contacted lengths of tubing 18 (bounded within l1 or l2) always maintain a round shape and become tangent to members 30a to 30d, (iii) and calculating angle θ from known distances L and x leaves three variables in solving $S(x)$, namely, $r_1(x)$, $r_2(x)$ and lc or contact length. Three equations relating $r_1(x)$, $r_2(x)$ and lc(x) accordingly allow $S(x)$ to be calculated.

In a first equation, angle θ from known distances L and x can be calculated as follows:

$$\theta = \arcsin\left(\frac{\frac{L}{\sqrt{2}} - x}{L}\right)$$

Knowing that L=l1+lc+l2, and that $$l_1 = r_1(x) ctg\theta$$

$$l_2 = r_2(x) tg\theta;$$

yields a first expression relating $r_1(x)$, $r_2(x)$ and lc(x), namely $$r_1(x)ctg\theta + lc(x) + r_2(x)tg\theta = L \quad \text{Equation 1}$$

A second equation relating $r_1(x)$, $r_2(x)$ and lc(x) is derived from the initial known radius R of tubing 18 in an uncompressed condition as seen in FIG. 3A $$2(\pi-2\theta)r_1(x) + 4lc(x) + 2(2\theta)r_2(x) = 2\pi R \quad \text{Equation 2}$$

A third relationship is made by assuming that the tubing cross-section area $(S(x))$ during the pumping will always keep the maximum value possible due to the elastic property of the material of tubing 18. That is, the tubing will expand to contact the inner surfaces of members 30a to 30d at all times. The tubing will attempt to consume as much area within the members as it can. Then in mathematics, the derivation of $S(x)$ to x will be equal to zero:

$$\theta = \arcsin(\cos 45° - x/L)$$

$$S(x) = (\pi-2\theta)r_1^2 + 2l(x)r_1 + (2\theta-2tg\theta/\cos 2\theta)r_2^2 + (4Ltg2\theta - 2l(x)\sin 2\theta)r_2 + 2Ltg\theta l(x) - 2L^2 \sin 2\theta tg\theta$$

$$\frac{dS(x)}{dx} = 0 \quad \text{Equation 3}$$

$$\frac{dS(x)}{dx} = \frac{d\theta}{dx}\left(-2r_1^2(x) + \left(\frac{2}{\cos^2\theta} + \frac{6\sin^2\theta}{\cos^4\theta}\right)r_2^2(x) + \left(\frac{8L\sin\theta}{\cos^3\theta} - 2l(x)\sin 2\theta\right)r_2(x) + \frac{2Ll(x)}{\cos^2\theta} - 4L^2\sin^2\theta - 2L^2 tg^2\theta\right) + \frac{dr_1(x)}{dx}(2l(x) + 2(\pi-2\theta)r_1(x)) + \frac{dr_2(x)}{dx}\left(\left(4\theta\frac{4\sin\theta}{\cos^3\theta}\right)r_2(x) + 4Ltg^2\theta - 2l(x)\sin^2\theta\right) + \frac{dl(x)}{dx}(2r_1(x) - 2r_2(x)\sin^2\theta + 2Ltg\theta)$$

The geometric shape of the inside of pump actuator 20 can accordingly be modeled by using the above three equations to solve for lc(x), $r_1(x)$ and $r_2(x)$ for any given value of x, which in turn yield $S(x)$, $\Delta S(x)$, $Q(x)$ and q(x,t). This is very useful to a "shuttle" type pump (e.g., elongated pump actuator 20 that surrounds tubing 18 to squeeze for pumping) because the output flow rate and volume for "shuttle" type pumps is calculated via shuttle movement cycle and the frequency of the cycle. The frequency of the cycle is indicative of flowrate, e.g., 1 ml/hr, 100 ml/hr, or 1200 ml/hr. Frequency accuracy is becomes more important as flowrate increases.

The flow within the cycle, or shuttle movement, is important to accuracy, especially for the low flow rate applications. Ideally, pump actuator 20 is moved to generate a linear pumping output, so that the output flowrate within the cycle can be controlled to be constant. If flowrate within each cycle is constant, then overall flowrate should be closer to constant, improving overall accuracy. Geometrically modeling the shape of the tubing during shuttle pumping as shown above allows the in-cycle flowrate to be controlled to be a constant.

The above modeling is stored and processed within logic implementer 12. Logic implementer 12 in turn controls the electronic signal to actuator 22 so that instantaneous flowrate q(x,t) is controlled to be a constant. In particular, it is contemplated to build a motion signal profile that varies Δx for a next time period based on a change in cross-sectional area ΔS(x) for that next time period to achieve a constant instant flowrate q(x,t) from time period to time period. ΔS(x) is determined via the modeling shown above.

Referring now to FIGS. 4A and 4B, actuator 40 illustrates an alternative embodiment for the pump actuator. Actuator 40 is similar to actuator 20 in certain respects, in that it uses four hinge members 46a to 46d to enclose a section l of tubing 18 in a diamond-shaped manner. Members 46a to 46d accordingly have the length l as shown in FIG. 1. Pump actuator 40 also includes linear actuator 22 and output shaft 24 as described above.

Output shaft 24 is connected to a bearing mount 42, which in turn is connected to a first hinge pin 44a. An embodiment for hinge members 46a to 46d and hinge pins 44a to 44d is shown in FIGS. 5 and 6. Hinge pin 44a hingedly connects hinge members 46a and 46b. Hinge pin 46b hingedly connects hinge members 46a and 46c. Hinge pin 44d hingedly connects hinge members 46b and 46d. Hinge members 46c and 46d are connected hingedly via bearing pin 44c, which in turn is connected to a member 34 that slides within a slot 38.

FIG. 4A shows pump actuator 40 in a fully retracted, pump-in end-of-stroke position. To push fluid out of tubing 18, linear actuator 22 causes output shaft 24 to extend towards fixture 36, compressing section l of tubing 18, and thereby forcing liquid through towards patient 80. FIG. 4B shows pump actuator 40 in an intermediate position, close to a full pump-out end-of-stroke position. Here again, pump actuator 40 attempts to flatten tubing 18 on the pump-out stroke as much as possible, so as to maximize pumping efficiency per stroke and to increase pumping accuracy (assuming the end-of-stroke pump-out volume in section l of tubing 18 to be zero). If pump actuator 40 is limited in how much it can flatten section l of tubing 18, the area S1 for the pump-out end of stroke is calculated and the extrapolated volume (S1×l) is used as the end of pump-out stroke volume instead of zero.

In FIGS. 2A to 2C and FIGS. 4A and 4B, the centers of tubing 18 remain fixed as illustrated. That is, the centers do not move up and down as output shaft 24 moves up and down because members 34b and 34 of actuators 20 and 40, respectively, move within respective slots 38b and 38 when the associated output shaft 24 moves. The pumping portion of tubing 18 lies in substantially the same line as surrounding portions of the tubing as seen in FIG. 1. This is advantageous because a bending moment is not placed on tubing 18, which could affect accuracy.

The in-cycle tubing geometry of tubing moved by actuator 40 can be modeled and implemented via logic implementer 12 in the same manner as shown above for actuator 20. This allows in-cycle flowrate to be controlled as a constant.

Referring now to FIGS. 5 and 6, one embodiment for hingedly connecting the hinge members 46a to 46d is illustrated. Hinge pins 44a to 44d are shown in descending order. The corresponding hinge member pairs, namely, hinges 46b and 46a, 46a and 46c, 46c and 46d, and 46d and 46b are shown correspondingly in descending order. As seen in FIG. 5, hinge members 46a to 46d are each notched at notch 52, so that a pair of members can be fitted together at alignment holes formed by a circular collar 54, as seen in FIG. 6.

Circular collar 54 in FIG. 6 is shown for the hinge members in order 46a, 46c, 46d and 46b. However, it should be appreciated from FIG. 5 that each of hinge members 46a to 46d includes a pair of circular collars, one of which appears in the lower left corner of the hinge member and the other of which appears in the upper right corner of the hinge member. That is, looking at FIG. 5, hinge member 46b actually appears twice, once in combination with hinge member 46a and in the second case in combination with hinge member 46d. In the top rung or pair of element numbers in FIG. 5, when hinge member 46b appears with hinge member 46a, the circular collar 54 for hinge member 46b appears in the upper right-hand corner of the hinge member. The second circular collar 54 for hinge member 46b appears in the lower left-hand corner of hinge member 46b when hinge member 46b is coupled alternatively with hinge member 46d in the final or lowest pair of element numbers in FIG. 5. Each of these hinge members 46a to 46d includes this alternating pattern of circular collars 54, such that each of the members can be hinged together to form a four-sided closed shape that can be compressed completely (see FIG. 6 showing that surfaces 1 and 2 can be bent upwards to mate with each other) to push liquid out of section l. The four-sided shape can then be opened to decompress tubing 18 to suck fluid into such section l of tubing 18.

It should be appreciated from FIG. 6 that the bend in the hinge collar 54 is placed on the outside of members 46a to 46d relative to surfaces 1 and 2 (as shown by arrows in which the members are to be bent), which allows surfaces 1 and 2 to come together flat against each other, allowing the pump-out stroke volume to be very close to zero. FIG. 5 also shows that the ends of hinge pins 44a to 44d can be connected to bearings 56a and 56b, which are in turn fixed to either bearing mount 42 or machine body 36 as seen in FIGS. 4A and 4B. Bearings 56a and 56b are replaced with caps (not seen) that prevent hinge pins 44b and 44d as seen in FIGS. 4A and 4B from coming loose from the abutting circular collars 54 of the associated hinge members.

FIG. 5 illustrates that a teflon or otherwise plastic or low friction material washer 58 can be sandwiched between mating circular collars 54. For example, if members 46a to 46d are metal, washer 58 prevents metal-to-metal contact, helping to reduce friction and noise. It is further contemplated to extend notches 52 away from circular collars 54 as seen in FIG. 5, such that the edges of the notches 52 do not rub against collars 54, again reducing friction and noise. Likewise, hinge pins 44a to 44d in an embodiment are made of a suitably strong material having a smooth exterior with a low coefficient of friction. If needed, hinge pins 44a to 44d can be coated or impregnated with a lubricant.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An infusion pump comprising:
an actuator having an output shaft;
a plurality of members, at least two of the members in a first hinged communication with the output shaft, and at least two of the members in a second hinged communication with each other, at least one of the first and second hinged communications formed via at least one hinge pin, such that the members at an output shaft actuated distance (x) create flat contact areas with tubing inserted within the members, and wherein remaining non-contact areas of the a tubing are at least substantially circular in shape; and
a logic implementer configured to use a calculated cross-sectional area of the tubing at the output shaft actuated distance (x) to control the actuator to obtain a desired flowrate.

2. The infusion pump of claim 1, wherein being configured to use the calculated cross-sectional area of the tubing at the output shaft actuated distance (x) includes using a motion profile that varies a change in the output shaft actuated distance (x) based on an expected change in the calculated cross-sectional area of the tubing to obtain the desired flowrate.

3. The infusion pump of claim 1, wherein the calculated cross-sectional area of the tubing is calculated knowing an angle (θ) of one of the members at the output shaft actuated distance (x) relative to a theoretical horizontal centerline of the tubing.

4. The infusion pump of claim 3, wherein the angle (θ) at the output shaft actuated distance (x) is common to each of the members.

5. The infusion pump of claim 1, wherein the calculated cross-sectional area of the tubing is calculated knowing a length of at least one of the members.

6. The infusion pump of claim 1, wherein the calculated cross-sectional area of the tubing is calculated knowing a nominal uncompressed radius or diameter of the tubing.

7. The infusion pump of claim 1, wherein the calculated cross-sectional area of the tubing has removed from it a cross-sectional thickness area of the tubing.

8. The infusion pump of claim 1, wherein the desired flowrate is a constant flowrate.

9. The infusion pump of claim 1, wherein the desired flowrate is based on a desired volume change, which is based on a desired change in the calculated cross-sectional area of the tubing multiplied by a constant length ($l_{actuator}$) of the members.

10. An infusion pump comprising:
   an actuator having an output shaft; a pump actuator having a plurality of members, at least two of the members in a first hinged communication with the output shaft, and at least two of the members in a second hinged communication with each other, at least one of the first and second hinged communications formed via at least one hinge pin
   the pump actuator having a length ($l_{actuator}$) moved by the output shaft and in contact with a tubing, such that the plurality of members of the pump actuator at an output shaft actuated distance (x) create flat contact areas with the tubing, and wherein remaining non-contact areas of the tubing are at least substantially circular in shape; and
   a logic implementer configured to use at least two relationships to solve for a same number of variables to calculate a cross-sectional area of the tubing at the output shaft actuated distance (x).

11. The infusion pump of claim 10, the logic implementer further configured to use the calculated cross-sectional area of the tubing at the output shaft actuated distance (x) to control the actuator to obtain a desired flowrate.

12. The infusion pump of claim 10, wherein one of the relationships is based on a constant length (L) of at least one member of the pump actuator.

13. The infusion pump of claim 10, wherein one of the relationships is based on a known uncompressed radius of the tubing.

14. An infusion pump comprising:
   an actuator having an output shaft;
   first and second members in a first hinged communication with the output shaft;
   a third member in a second hinged communication with the first member;
   a fourth member in a third hinged communication with the second member, at least one of the first, second, and third hinged communications provided via at least one hinge pin; and
   the third and fourth members held mechanically such that when the actuator is actuated in a first direction, a tube section extending through the members is compressed to expel a fluid from the tube section and when the actuator is actuated in a second direction, the tube section is decompressed to draw fluid into the tube section.

15. The infusion pump of claim 14, wherein the actuator is extended in the first direction and retracted in the second direction.

16. The infusion pump of claim 14, wherein the first member is in the second hinged communication with the third member via a slide member, the slide member held slideably within a restraint.

17. The infusion pump claim 14, wherein the second member is in the third hinged communication with the fourth member via a slide member, the slide member held slideably within a restraint.

18. The infusion pump of claim 14, wherein the third member is in a fourth hinged communication with the fourth member.

19. The infusion pump of claim 18, wherein the third member is in the fourth hinged communication with the fourth member via a slide member, the slide member held slideably within a restraint.

20. The infusion pump of claim 14, wherein the members have a depth, the depth at least substantially defining a length of the tube section.

21. The infusion pump of claim 14, wherein at least one of: (i) the third member is hinged directly to the first member, (ii) the fourth member is hinged directly to the second member, and (iii) the third member is hinged directly to the fourth member.

22. The infusion pump of claim 14, wherein the third member is hinged directly to the fourth member at a location fixed to a restraint.

* * * * *